United States Patent [19]

Ries

[11] 4,066,083
[45] Jan. 3, 1978

[54] STERILE SURGICAL COLLAGEN PRODUCT

[75] Inventor: Peter E. Ries, Reinach, Basel-Land, Switzerland

[73] Assignee: Pentapharm A.G., Basel, Switzerland

[21] Appl. No.: 692,542

[22] Filed: June 3, 1976

[51] Int. Cl.² .................... A61F 13/00; A61L 15/04
[52] U.S. Cl. .................................. 128/325; 8/127.5;
128/92 C; 128/334 R; 128/296; 128/DIG. 8;
195/6
[58] Field of Search ............. 195/4, 5, 6; 128/156,
128/296, 334 R, 335.5, DIG. 8, 325, 92 C;
8/94.11, 94.15, 127.5; 424/27; 260/112 R, 123.7

[56] References Cited

U.S. PATENT DOCUMENTS

| 2,039,262 | 4/1936 | Schulte | 128/335.5 |
|---|---|---|---|
| 2,202,566 | 5/1940 | Schulte | 128/156 |
| 3,034,852 | 5/1962 | Nishihara | 195/6 X |
| 3,121,049 | 2/1964 | Nishihara | 195/6 |
| 3,314,861 | 4/1967 | Fujii | 195/6 |
| 3,491,760 | 1/1970 | Braun et al. | 128/335.5 |
| 3,587,586 | 6/1971 | Kronenthal | 128/334 |

FOREIGN PATENT DOCUMENTS

| 1,385,319 | 2/1975 | United Kingdom | 195/6 |

OTHER PUBLICATIONS

Rose et al "Condensed Chemical Dictionary" Van Nostrand Reinhold Publisher Co. 1970, p. 676.

*Primary Examiner*—R. B. Penland
*Attorney, Agent, or Firm*—Pennie & Edmonds

[57] ABSTRACT

A sterile surgical collagen product which has a felt or fleece-like structure and which exerts a haemostatic action, has a high absorption capacity for body fluids, promotes the regeneration of tissues, is highly resorptive, has substantially no antigenic activity and has optimum mechanical properties so as to make it suitable for being applied to or introduced into wounds or into bone cavities.

2 Claims, No Drawings

STERILE SURGICAL COLLAGEN PRODUCT

BACKGROUND OF THE INVENTION

The invention relates to the art of surgical materials to be used for healing wounds, more particularly to a sterile collagen product and to its preparation from animal collagen.

As is known, collagen products prepared from animal tissues are used as wound coverings or adhesives. British Pat. No. 1,147,072 relates to a wound covering consisting of a tanned collagen sponge and collagen covering film applied to one side of the sponge. South African Pat. No. 6,705,871 relates to a collagen product which consists of microcrystalline colloidal collagen and which is to be used as a mixing component together with other active substances in cosmetic and pharmaceutical preparations. A further commercially available collagen product consists of a light flocculent powder which, though haemostatically active, is difficult to apply in depth into a wound and which has the disadvantage of being washed away by strong diffuse bleedings.

In order to obtain optimum results in wound healing by means of collagen, a collagen product would have to be available which should meet all the requirements specified hereinafter:

1. it should have a high haemostatic activity;
2. it should have a high absorption capacity for body fluids;
3. it should promote the regeneration of tissues, especially of bone tissues;
4. it should have a high resorbability;
5. it should have as low an antigenic activity as possible; and
6. it should have optimum mechanical properties so as to make it suitable for the application to or the introduction into wounds or into bone cavities.

The prior art collagen products either described in the literature or available on the market, while meeting one or a restricted number of the requirements set forth above, do not meet all of them at the same time.

SUMMARY OF THE INVENTION

An object of the invention is to provide a surgical collagen product having a felt or fleece-like structure with open, communicating voids between the fibres.

A further object of the invention is to provide a surgical collagen product having a high haemostatic activity, a high absorption capacity for body fluids, the property of promoting the regeneration of tissues, especially of bone tissues, a high resorbability, as low an antigenic activity as possible and optimum mechanical properties to make it suitable for the application to or the introduction into wounds or into bone cavities.

The collagen product of this invention is obtained by improvements of methods known in the art. The general method for obtaining the collagen product consists in degreasing collagen-containing tissues of slaughtered animals, extracting the degreased tissues with electrolyte solutions for removing non-collagen type ballast substances, treating the obtained tissue with proteolytic enzymes which do not attack the basic structure of collagen in order to remove non-collagen type proteinaceous accompanying substances and telopeptides, purifying the crude collagen by reprecipitation, desalting the purified collagen, dissolving the purified and desalted collagen in an aqueous medium, freeze-drying the collagen and sterilizing the dried collagen.

In order to obtain a collagen product having the properties specified above the degreasing of the animal tissue and the removal therefrom of the undesirable water-soluble ballast substances are carried out simultaneously by extracting the tissue with about the five-fold volume of 5 to 15% aqueous sodium chloride solution containing about 0.2 to 1 part by weight of sodium azide as a preserving agent per 1000 parts by weight of the said solution and 0.5 to 2% by weight of a non-ionic fat-dispersing agent.

DETAILED DESCRIPTION OF THE INVENTION

The starting materials used for preparing the collagen product of this invention can be skins, tendons or bones of slaughtered animals, e.g. pigs or bovine animals.

The collagen-containing tissue, e.g. pig skin, is finely comminuted at temperatures not exceeding 40° C. Prior to comminuiting the tissue is cooled to $-10°$ to $-20°$ C. The tissue pulp is then extracted with about the five-fold volume of 5 to 10%, preferably 10%, aqueous sodium chloride solution containing 0.1 to 1 part by weight of sodium azide as a preserving agent per 1000 by weight of said solution and 0.5 to 2% by weight of a non-ionic fat-dispersing wetting agent. By this extraction the undesirable water-soluble ballast substances and the greasy components are removed from the tissue. Wetting agents which can be used as a dispersing agent include the detergents commonly used for household purposes. Compared to the commonly used organic preserving agents, sodium azide has the advantage of being easily soluble in water and thus capable of being easily removed by washing. The extraction is repeated, e.g. twice.

The degreased fibrous tissue pulp is washed with water or 0.1 to 5% aqueous formic, acetic or citric acid, or another similar aliphatic acid, preferably with 3% aqueous acetic acid, and then digested at a pH of about 2.5 to 3.5 in the five-fold volume of 0.1 to 5%, preferably 3% aqueous acetic acid containing about 1 part by weight of a proteolytic enzyme, preferably pepsin, and about 1 part by weight of chloroform as a preserving agent per 1000 parts by weight of the tissue used as starting material. By this treatment the non-collagen type accompanying substances and the telopeptides, which are mainly responsible for the antigenicity of collagen, are removed without the filamentous collagen molecules being split into smaller peptide fragments. After a digestion time of about 8 to 48 hours the homogeneous, highly viscous collagen suspension is filtered through a suction filter having a sintered glass bottom or a stainless steel wire sieve. The collagen is then precipitated from the viscous filtrate by the addition of saturated aqueous sodium chloride solution in a quantity such that the sodium chloride concentration in the suspension is about 3 to 5%. The pepsin remaining in the reaction mixture is inactivated by adjusting the pH of the collagen suspension to about 8.6 to 8.8 by means of an aqueous alkali metal hydroxide solution, preferably a sodium hydroxide solution.

After about ½ to 1 hour the obtained crude collagen is separated by centrifugation. The crude collagen is purified by dissolution in a 0.05 to 5% aqueous solution of one of the organic acids mentioned above, preferably in 3% aqueous acetic acid, and by precipitation with sodium or potassium chloride. The precipitated collagen is again separated by centrifugation. This purification procedure is preferably repeated. The purified collagen is then desalted by washing with 60 to 75, preferably 70% by volume aqueous ethyl alcohol until the salt content of the collagen is reduced to 0 to 0.9% by weight, calculated on the weight of the dry residue of the collagen pulp. The desalted pure collagen is centrifuged or filtered on a suction filter in order to remove excess ethyl alcohol. Small quantities of residual alcohol would be detrimental to the further processing of the collagen. The collagen can also be desalted by ultrafiltration or dialysis.

The purified and desalted collagen is dissolved in demineralized or distilled water, to which up to 3% by weight of formic or acetic acid may be added, in a concentration corresponding to about 0.5 to 2% by weight of dry residue. The aqueous collagen is then freeze-dried. The dried collagen can be packed in plastic bags, e.g. in polyethylene bags, which are heat-sealed. The packed collagen product is sterilized by irradiating it through the bag walls with a dose of about 2 to 3.5 millirad of $\gamma$-rays.

Depending on the shape of the vessel in which the collagen is freeze-dried the collagen product can be obtained in the form of discs or of square or rectangular slabs.

The collagen product of this invention has a felt or fleece-like fibrous structure wherein the voids or interstices between the fibres are communicating. As a result of this structure the collagen product has a high absorptive capacity for body fluids. Furthermore, it is flexible and can be easily cut into pieces having the desired shape and dimensions. It can be easily applied on or introduced into wounds ad can be used as coverings which are fixed on wounds by means of surgical adhesives. The collagen product of this invention also has a high haemostatic activity and is easily resorbed. It is capable of promoting to a high extent the regeneration of tissues, especially of bone tissues which is particularly important in surgical orthopaedy. Experiments performed so far with the collagen product have shown that the collagen product has practically no antigenic activity.

The collagen product of this invention can generally be used with advantage for the superficial covering of wounds in order to promote wound healing and to protect the wound against infections and dehydration. Moreover, it can be used as a haemostatic agent in parenchymatous bleedings, as a carrier of surgical adhesives for binding tissues and as a filling material for pathological bone cavities. It replaces the spongioplastic interventions in surgical orthopaedy.

The commercially available collagen products are completely unsuited for this purpose. The collagen product of this invention is conveniently used in the following cases: treatment of ulcera, treatment of burns, haemostasis in thorax surgery, in liver and spleen injuries and in prostatectomies, gluing of sutures of blood vessels and disrupted parenchymatous tissues which are difficult to stitch.

Prior to its application the collagen product can be soaked or charged with pysiologically active substances such as antibiotics, disinfectants, physiological salt solution, local anaesthetics, etc.

The invention is further illustrated by the following working examples.

EXAMPLE 1

1 kg of pig skin was frozen at $-10°$ to $-b\ 20°$ C and then finely commminuted by means of a high speed knive homogeneizer. The temperature of the skin materials was kept below 40° C by adding pieces of ice. The viscous fibrous tissue pulp thus obtained was suspended, while vigorously stirring, in 5 liters of 10% aqueous sodium chloride solution containing 2.5g of sodium azide and 50 m$l$ of a 10% aqueous solution of the non-ionic wetting agent NP 55/52 (polyoxyethylene nonyl phenyl ether). The suspension was stirred for a further 2 hours and then centrifuged. The grayish or brownish turbid supernatant phase containing fats and undesirable water-soluble accompanying ballast substances was discarded. The residual white skin fiber pulp was further extracted twice in the same manner, except that 0.1 mole of disodium hydrogenophosphate was added to the extraction fluid.

The remaining skin fiber pulp was stirred in 3% aqueous acetic acid and centrifuged. The solid centrifugate was suspended in 5 liters of 3% acetic acid containing 1 g of pepsin and 5 ml of chloroform. The suspension was allowed to stand overnight at room temperature. The proteolyzed viscous colorless, slightly milky collagen suspension was filtered through a fine stainless steel wire sieve in vacuo.

Saturated aqueous sodium chloride solution was added slowly, while stirring, to the viscous filtrate until the sodium chloride content of the mixture was about 5%. The collagen separated in the form of a fibrous, flocculent white precipitate. The residual traces of pepsin were inactivated by treating the precipitate with 500 ml of 30% aqueous sodium hydroxide for 2 hours.

The collagen was separated by centrifugation, dissolved in 5 liters of 3% aqueous acetic acid at pH 3 to 4, precipitated by the addition of saturated aqueous sodium chloride solution and again separated by centrifugation. This procedure was repeated twice.

The sodium chloride containing residue was stirred together with about 70% aqueous ethyl alcohol for half an hour. The mixture was then centrifuged. These operations were repeated until the separated collagen had a sodium chloride content of 0.06%, calculated on the weight of the dry residue.

The purified and desalted collagen was dissolved in 3 volumes of 10% acetic acid and diluted with distilled water (about 2.5 to 5 fold volume) until the collagen concentration of the solution corresponded to a dry residue of 1%. The viscous collagen solution was filtered through a G1 suction filter having a sintered glass bottom. The filtrate was poured into circular glass dishes and freeze-dried. 0.5 cm thick collagen discs were thus obtained which had a felt or fleece-like structure. The collagen discs were packed into polyethylene bags which were heat-sealed. The packed collagen discs were sterilized by irradiation with a dose of 2.5 millirad of $\gamma$-rays.

EXAMPLE 2

A degreased and extracted fibrous tissue pulp obtained by the method described in Example 1 from 1 kg of bovine tendons was suspended in 5 volumes of 0.5 M acetic acid. To the suspension a solution of 1 g of technical pepsin in 100 ml of 0.01 N HCl was added. The pH of the suspension was adjusted to 2.9 with HCl. The suspension was digested for 48 hours at room temperature, while it was repeatedly stirred. The viscous collagen suspension thus obtained was filtered through a G 1 suction filter in order to remove non-digested residues. The collagen was precipitated from the suspension by the addition of 30% aqueous sodium hydroxide solution and separated by centrifugation. The collagen was purified by dissolution in 0.5 M acetic acid and precipitation by adding slowly 3% aqueous sodium chloride solution. The purified collagen was dissolved in 0.5 M acetic acid and diluted with water. The residual sodium chloride present in the collagen was removed by washing on an ultrafilter. The ultrafiltration was continued until no more chloride ions were detected in the eluate by silver nitrate and the collagen concentration was 0.5%. The collagen solution was filtered and freeze-dried, and the freeze-dried collagen was packed and sterilized in the manner described in Example 1. 102 g of a collagen fleece were obtained.

I claim:

1. A method for preparing a surgical collagen product which has a felt- or fleece-like structure with open, communicating voids between the collagen fibers, comprising comminuting collagen-containing tissues of pigs at a temperature not exceeding 40° C, degreasing the resulting tissue pulp and simultaneously removing therefrom undesirable water-soluble non-collagen ballast substances by repeatedly treating the said tissue pulp with about a five-fold volume, based on the pulp volume, of a 5 to 15% aqueous sodium chloride solution containing about 0.2 to 1 part by weight of sodium azide as a preserving agent per 1000 parts by weight of the said solution and 0.5 to 2% by weight of a non-ionic fat-dispersing wetting agent, washing the resulting fiber pulp with water or 0.1 to 0.5% aqueous formic, acetic or citric acid, digesting the fiber pulp for 8 to 48 hours at a pH of about 2.5 to 3.5 in the five-fold volume, based on the volume of the pulp, of 0.1 to 5% aqueous acetic acid containing about 1 part by weight of pepsin per 1000 parts by weight of the tissue used as the starting material in order to remove non-collagen type proteinaceous substances and telopeptides, precipitating collagen from the resulting collagen suspension by the addition thereto of aqueous sodium chloride in such a quantity that the sodium chloride concentration of the suspension is about 3 to 5%, separating the precipitated collagen and desalting it by ultrafiltration, dialysis or washing with 60 to 75% aqueous ethyl alcohol until the salt content of the collagen is reduced to 0 to about 0.9% by weight, calculated on the weight of the dry collagen, dissolving the desalted collagen in demineralized or distilled water containing up to 3% by weight of a strong organic acid in such a proportion that the concentration of collagen in the resulting solution corresponds to a dry residue of about 0.5 to 2% by weight, freeze-drying the collagen solution, and sterilizing the freeze-dried collagen product.

2. A sterile surgical collagen product having a felt- or fleece-like structure with open, communicating voids between the fibers, as obtained by the method according to claim 1.

* * * * *

UNITED STATES PATENT AND TRADEMARK OFFICE
CERTIFICATE OF CORRECTION

PATENT NO. : 4,066,083
DATED : January 3, 1978
INVENTOR(S) : Peter E. Ries

It is certified that error appears in the above-identified patent and that said Letters Patent are hereby corrected as shown below:

Column 4, line 1, reads "-10 to -b20°C", and should read -10 to -20°C

Signed and Sealed this

Ninth Day of May 1978

[SEAL]

Attest:

RUTH C. MASON
Attesting Officer

LUTRELLE F. PARKER
Acting Commissioner of Patents and Trademarks

UNITED STATES PATENT AND TRADEMARK OFFICE
CERTIFICATE OF CORRECTION

PATENT NO. : 4,066,083
DATED : January 3, 1978
INVENTOR(S) : Peter E. Ries

It is certified that error appears in the above-identified patent and that said Letters Patent are hereby corrected as shown below:

Column 3, line 10, reads "would be detrimental", should read --would not be detrimental--

Column 3, line 22, reads "millirad", should read --megarad--

Column 4, line 57, reads "millirad", should read --megarad--

Signed and Sealed this

Eleventh Day of July 1978

[SEAL]

Attest:

RUTH C. MASON
Attesting Officer

DONALD W. BANNER
Commissioner of Patents and Trademarks